United States Patent [19]
Henry et al.

[11] Patent Number: 5,840,752
[45] Date of Patent: Nov. 24, 1998

[54] REDUCTION OF HAIR GROWTH

[76] Inventors: James P. Henry, 10257 Meadow Fence Ct., Myersville, Md. 21773; Gurpreet S. Ahluwalia, 8632 Stableview Ct., Gaithersburg, Md. 20882; Douglas Shander, 16112 Howard Landing Dr., Gaithersburg, Md. 20878

[21] Appl. No.: 754,556

[22] Filed: Nov. 21, 1996

[51] Int. Cl.$^6$ ..................................................... A61K 31/35
[52] U.S. Cl. .......................... 514/460; 514/419; 514/569; 514/345
[58] Field of Search .................................... 514/455, 460, 514/419, 569, 345

[56] References Cited

U.S. PATENT DOCUMENTS

| | | |
|---|---|---|
| 3,426,137 | 2/1969 | Philpitt et al. . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glea . |
| 4,269,831 | 5/1981 | Ferrari et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Brener et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,474,763 | 12/1995 | Shander et al. . |
| 5,554,608 | 9/1996 | Ahluwalia et al. . |

FOREIGN PATENT DOCUMENTS

| | | |
|---|---|---|
| 0413528A1 | 10/1990 | European Pat. Off. . |
| 0532219A2 | 9/1992 | European Pat. Off. . |
| 1 458 349 | 12/1976 | United Kingdom . |
| WO 96/08248 | 3/1996 | WIPO . |

OTHER PUBLICATIONS

Smythe, C.D.W. and Kealey, T., HMG–CoA reductase activity and regulation in the isolated human hair follicle Inter. Congr. Ser. (1996), 1111 (Hair research for the next millenium), 413–416.

Harmon et al., British Journal Of Dermatology, "Hair Fibre Production by Human Hair Follicles in Whole–organ Culture," 415–423, 1994.

Harmon et al., SID Abstracts, "12–0–Tetradecanoylphorbol–12–Acetate Inhibits Human Hair Follicle Growth and Hair Fiber Production in Whole–organ Cultures," 102:533 1994.

Philpott et al., Journal Of Dermatological Science, "Human Hair Growth in vitro: A Model for the Study of Hair Follicle Biology," 7:s55–s72, 1994.

Harrison's Principles Of Internal Medicine "Part Seven Disorders of the Cardiovascular System", 1108–17, 1994.

Procopiou et al., J. Med. Chem. The Squalestatins: Novel Inhibitors of Squalene Synthase. Enzyme Inhibitory Activities and in Vitro Evaluation of C1–Modified Analogues, 3274–81, 1994.

Jindo et al., The Journal Of Dermatology, "Organ Culture of Mouse Vibrissal Hair Follicles in Serum–free Medium," 20:756–762, 1993.

Messenger, The Society For Investigative Dermatology, "The Control of Hair Growth: An Overview," 1011:4s–9s, 1993.

Li et al., Proc. Natl. Acad. Sci. USA "Hair Shaft Elongation, Follicle Growth, and Spontaneous Regression in Long–term, Gelatin Sponge–supported Histoculture of Human Scalp Skin," 89:8764–8768, 1992.

Li et al., In Vitro Cell. Dev. Biol., "Skin Histoculture Assay for Studying the Hair Cycle," 28A:695–698, 1992.

Salzer et al., Pharmacology Hear. Res., "Cochlear Damage and Increased Threshold in Alpha–difluoromethylornithine DFMO Treated Guinea Pigs," 451–2:101–112, 1990 Abstract.

Grundy, The New England Journal Of Medicine, HMG–CoA Reductase Inhibitors for Treatment of Hypercholesterolemia, 24–32, 1988.

Goos et al., Arch. Dermatol. Res., "An Improved Method for Evaluating Antiandrogens," 273:333–341, 1982.

Johnson et al., Biochemistry, "Inhibition of Hexokinase and Protein Kinase Activities of Tumor Cells by a Chloromethyl Ketone Derivative of Lactic Acid," 2112:2984–2989, 1982.

Simpson et al., British Journal Of Dermatology, "The Effect of Topically Applied Progesterone on Sebum Excretion Rate," 100:687–692, 1979.

Lehninger, Biochemistry, "The Molecular Basis of Cell Structure and Function", 678–86, 1979.

Brannan et al., Journal Of Lipid Research, "3–Hydroxy–3methylglutaryl coenzyme A reductase activity in human hair roots", 7–11, 1975.

Sato, Biology And Disease Of The Hair, "The Hair Cycle and its Control Mechanism," 3–13, 1976.

Adachi et al., J. Soc. Cosmet. Chem., "Human Hair Follicles: Metabolism and Control Mechanisms," 21:901–924, 1970.

*Primary Examiner*—Keith D. MacMillan
*Attorney, Agent, or Firm*—Fish & Richardson P.C.

[57] ABSTRACT

Mammalian hair growth is reduced by applying to the skin an inhibitor of a cholesterol synthetic pathway enzyme.

32 Claims, No Drawings

REDUCTION OF HAIR GROWTH

The invention relates to reducing hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Cholesterol in cells is synthesized from acetyl CoA according to the following biochemical pathway:

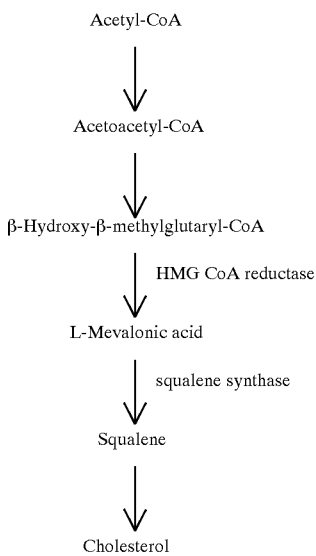

One important enzyme in cholesterol synthesis is (hydroxymethyl-glutaryl-CoA reductase (HMG CoA reductase), which assists in the conversion of β-hydroxy-β-methylglutaryl-CoA to L-mevalonic acid. A second enzyme, squalene synthase, is involved in the conversion of L-mevalonic acid to squalene. Inhibitors of the enzyme HMGCOA reductase have been found to be effective in reducing cholesterol, and several are used therapeutically in patients with increased risk for atheroscerotic vascular disease due to hypercholesterolemia.

The enzymes involved in the just described biochemical pathway will be referred to herein as the "cholesterol synthetic pathway enzymes." It has now been found that unwanted mammalian (including human) hair growth—particularly androgen-stimulated hair growth—can be reduced by applying to the skin a composition including an inhibitor of a cholesterol synthetic pathway enzyme, e.g., HMGACoA reductase and squalene synthetase, in an amount effective to reduce hair growth. The unwanted hair growth which is reduced may be normal hair growth, or hair growth that results from an abnormal or diseased condition.

Inhibitors of HMGCoA reductase include fluvastatin ([R*,S*-(E)]-(±)-7-[3-(4-fluorophenyl-1-(1-methylethyl-1-H-indol-2-yl]-3,5-dihydroxy-6-heptanoic acid); sinvastatin (1S-[1α,3α,7β,8β(2S*,4S*),8aβ]]-1,2,3,7,8,8a-hexahydro-3,7-dimethyl-8-[2-tetrahydro-4-hydroxy-6-oxo-2H-pyran-2-yl)ethyl]-1-napthalenyl-2,2-dimethyl-butanoic acid); lovastatin(1S-[1S-[1α(R*),3α,7β,8β(2S*,4S*),8αβ]]-1,2,3,7,8,8a-hexahydro-3,7-dimethyl-8-[2-(tetrahydro-4-hydroxy-6-oxo-2H-pyran-2-yl)ethyl]-1-naphthalenyl 2-methylbutanoate; mevinolin (1,2,6,7,8,8a-hexahydro-β-δ-dihydroxy-2,6-dimethyl-8-(2α-methyl-1-oxobutoxy-1-naphthalene-heptanoic acid lactone); pravastatin (1S-[1α(BS*,δS*)2α,6α,8β(R*),8aα]]-1,2,6,7,8,8a-hexahydro-β,δ,6-trihydroxy-2-methyl-1-oxbutoxy-1-naphthalene-heptanoic acid); 4α-ethyl-5α-cholest-7-ene-3β,15α-diol; 25-hydroxycholesterol; 26-aminocholesterol; 27-hydroxycholesterol; 7β-hydroxycholesterol; rivastatin; and mevastatin; and 7-ketocholesterol (5-cholesten-3β-Ol-7-one).

Inhibitors of squalene synthetase include squalestatin (zaragozic acid) and squalestatin analogs. See Procopiou, P. A., Bailey, E. J., et al. J. of Medicinal Chemistry, vol. 37, 3274–3281, 1994.

The inhibitors of a cholesterol synthetic pathway enzyme preferably are incorporated in a topical composition which preferably includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an inhibitor of a cholesterol synthetic pathway enzyme, the flank organs of each of a group of hamsters are depilated by applying a thioglycolate based chemical depilatory (Surgex) and/or shaved. To one organ of each animal 10 $\mu$l. of vehicle alone once a day is applied, while to the other organ of each animal an equal amount of vehicle containing an inhibitor of a cholesterol synthetic pathway enzyme is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 15%, more preferably at least about 40%, and most preferably at least about 60% when tested in the Golden Syrian hamster assay. A number of inhibitors of cholesterol a synthetic pathway enzyme were tested in the Golden Syrian hamster assay; the results are provided in Table 1:

TABLE 1

| Compound | Dose | Vehicle | Hair Mass (mg) ± SEM Treated | Control | % Reduction |
|---|---|---|---|---|---|
| Lovastatin | 10% | A | 0.81 ± 0.13 | 2.14 ± .19 | 63±4 |
| Simivistatin | 10% | A | 0.60 ± 0.11 | 1.62 ± .27 | 61 ± 7 |
| 7-Ketocholesterol | 10% | C | 1.01 ± 0.1 | 2.23 ± .33 | 54 ± 7 |
| Mevastatin | 5% | B | 1.09 ± 0.07 | 1.40 ± .13 | 19 ± 7 |
| 25-Hydroxy-cholesterol | 5% | C | 1.04 ± 0.10 | 1.29 ± .13 | 17 ± 9 |

Vehicle A: 40% acetone, 40% dipropylene glycol, 20% dimethyl sulfoxide
Vehicle B: 100% dimethyl sulfoxide
Vehicle C: 85% dimethyl sulfoxide, 10% benzyl alcohol, 5% NMP Four hamster flank organs rich in hair follicles were sonicated in 250 $\mu$l of Buffer A (0.1 M sucrose, 0.055M potassium chloride, 0.04M potassium phosphate, and 0.03M potassium EDTA, pH 7.2). Cell debris were removed by two 15 minute centrifugations at 10,000×g. The supernatant was centrifuged at 100,000×g for 45 minutes. The pellet containing the microsomes was resuspended in Buffer B (Buffer A containing 10 mM DTT). The resuspended microsomes were frozen overnight at −20° C.

The microsomes were allowed to thaw at either room temperature or 37° C. and an equal volume of Buffer C (Buffer A containing 50% glycerol and 10 mM DTT) was added to the microsome solution. The suspension was rehomogenized with 10 downward passes of a hand held homogenizer and incubated at 37° C. for 60 minutes. The suspension was diluted 3 fold with Buffer B that had been preheated to 37° C. for 60 minutes. The suspension was homogenized a second time with an additional 10 downward passes of the hand held homogenizer. The homogenate was centrifuged a final time at 100,000×g for 60 minutes, and the supernatant was used in a HMGCoA reductase assay.

The reductase activity was measured in reaction mixture containing Buffer B with 3.5 $\mu$mol NaCl, 5 $\mu$mol glucose-6-phosphate, 1 $\mu$mol NADP, 2.2 units glucose-6-phosphate dehydrogenase, and 150 nmol 3-[$^{14}$C]-HMGCoA (0.34 Ci/mol), pH 7.2. The microsomal protein is added to a final concentration of 0.4–1 mg/ml. The reaction was stopped with the addition of 50 $\mu$l of 33% KOH. After 30 minutes 25 $\mu$l of bromophenol blue (0.05%) was added, followed by 105–110 $\mu$l of 5N HCL until a yellow color change occurred. The sample was again incubated for 30 minutes at the acidic pH, and the precipitated proteins was removed by centrifugation. The supernatant was applied to a AG-1-X8 formate column (0.7×10 cM) in $H_2O$. 1.8 ml of water was used to wash the column and is discarded. The product of the reaction, [$^{14}$C]mevalonolactone, was collected in the next 5 ml wash, and the radioactivity determined by scintillation counting.

This assay was used to measure the inhibition of HMG CoA reductase activity in extracts of hair follicles isolated from the hamster flank organ after a 1 hour incubation with and without the presence of an enzyme inhibitor. More preferred inhibited HMG CoA reductase activity by at least 50%, and the most preferred inhibitors inhibited HMG CoA reductase activity by at least 80%, when tested at 14 $\mu$M. Lovastatin and simivistatin were tested at 14 $\mu$M and gave almost complete inhibition of the enzyme activity, 97% and 100%, respectively.

Other embodiments are within the claims.

We claim:

1. A method of reducing mammalian hair growth which comprises selecting an area of skin from which reduced hair growth is desired; and applying to said area of skin a dermatologically acceptable composition comprising an inhibitor of a cholesterol pathway enzyme in an amount effective to reduce hair growth.

2. The method of claim 1, wherein said inhibitor comprises fluvastatin.

3. The method of claim 1, wherein said inhibitor comprises simvastatin.

4. The method of claim 1, wherein said inhibitor comprises lovastatin.

5. The method of claim 1, wherein said inhibitor comprises mevinolin.

6. The method of claim 1, wherein said inhibitor comprises pravastatin.

7. The method of claim 1, wherein said inhibitor comprises 4-α-ethyl-5α-cholest-7ene-3β,15α-diol.

8. The method of claim 1, wherein said inhibitor comprises 25-hydroxy cholesterol.

9. The method of claim 1, wherein said inhibitor comprises 26-aminocholesterol.

10. The method of claim 1, wherein said inhibitor comprises 27-hydroxycholesterol.

11. The method of claim 1, wherein said inhibitor comprises rivastatin.

12. The method of claim 1, wherein said inhibitor comprises mevastatin.

13. The method of claim 1, wherein said inhibitor comprises squalestatin.

14. The method of claim 1, wherein said inhibitor comprises an analogue of squalestatin.

15. The method of claim 1, wherein said inhibitor is an inhibitor of HMGCoA reductase.

16. The method of claim 1, wherein said inhibitor is an inhibitor of squalene synthetase.

17. The method of claim 1, wherein the concentration of said inhibitor of in said composition is between 1% and 30%.

18. The method of claim 1, wherein the composition provides a reduction in hair growth of at least 15% when tested in the Golden Syrian hamster assay.

19. The method of claim 1, wherein the composition provides a reduction in hair growth of at least 40% when tested in the Golden Syrian hamster assay.

20. The method of claim 1, wherein the composition provides a reduction in hair growth of at least 60% when tested in the Golden Syrian hamster assay.

21. The method of claim 1, wherein the inhibitor is applied to the skin in an amount of from 10 to 3000 micrograms of said inhibitor per square centimeter of skin.

22. The method of claim 1, wherein said mammal is a human.

23. The method of claim 22, wherein said area of skin is on the face of the human.

24. The method of claim 22, wherein said area of skin is on a leg of the human.

25. The method of claim 22, wherein said area of skin is on an arm of the human.

26. The method of claim 22, wherein said area of skin is in an armpit of the human.

27. The method of claim 22, wherein said area of skin in on the torso of the human.

28. The method of claim 22, wherein said human is a woman suffering from hirsutism.

29. A method of reducing mammalian hair growth which comprises selecting an area of skin from which reduced hair growth is desired; and applying to said area of skin a dermatologically acceptable composition comprising an inhibitor of HMGCoA reductase in an amount effective to reduce hair growth.

30. A method of reducing mammalian hair growth which comprises selecting an area of skin from which reduced hair growth is desired; and applying to said area of skin a dermatologically acceptable composition comprising an inhibitor of squalene sythetase in an amount effective to reduce hair growth.

31. A method of reducing mammalian hair growth which comprises selecting an area of skin from which reduced hair growth is desired; and applying to said area of skin a dermatologically acceptable composition comprising an inhibitor of a cholesterol pathway enzyme other than HMGCoA reductase and squalene synthetase in an amount effective to reduce hair growth.

32. A method of reducing mammalian hair growth which comprises selecting an area of skin from which reduced hair growth in desired; and inhibiting a cholesterol pathway enzyme in said area of skin sufficiently to cause a reduction in hair growth in said area of skin.

* * * * *